United States Patent
Darricau et al.

(10) Patent No.: US 10,450,591 B2
(45) Date of Patent: Oct. 22, 2019

(54) BACTERIAL STRAINS FOR THE PRODUCTION OF VANILLIN

(71) Applicant: LESAFFRE ET COMPAGNIE, Paris (FR)

(72) Inventors: Mylène Darricau, Balanson (FR); Thomas Desfougeres, Neuville en Ferrain (FR); Jean-Luc Pernodet, Cachan (FR)

(73) Assignee: LESAFFRE ET COMPAGNIE, Paris (FR)

( * ) Notice: Subject to any disclaimer, the term of this patent is extended or adjusted under 35 U.S.C. 154(b) by 0 days.

(21) Appl. No.: 15/763,564

(22) PCT Filed: Sep. 22, 2016

(86) PCT No.: PCT/FR2016/052403
§ 371 (c)(1),
(2) Date: Mar. 27, 2018

(87) PCT Pub. No.: WO2017/055712
PCT Pub. Date: Apr. 6, 2017

(65) Prior Publication Data
US 2018/0320204 A1 Nov. 8, 2018

(30) Foreign Application Priority Data

Sep. 29, 2015 (FR) ...................................... 15 59142

(51) Int. Cl.
| | |
|---|---|
| *C12P 7/26* | (2006.01) |
| *C12N 1/20* | (2006.01) |
| *C07C 47/58* | (2006.01) |
| *C12N 9/88* | (2006.01) |
| *C12P 7/24* | (2006.01) |
| *C12N 15/74* | (2006.01) |
| *C12N 9/00* | (2006.01) |

(52) U.S. Cl.
CPC .............. *C12P 7/26* (2013.01); *C07C 47/58* (2013.01); *C12N 1/20* (2013.01); *C12N 9/88* (2013.01); *C12N 9/93* (2013.01); *C12N 15/74* (2013.01); *C12P 7/24* (2013.01); *C12Y 401/02041* (2013.01); *C12Y 402/01101* (2013.01); *C12Y 602/01034* (2013.01)

(58) Field of Classification Search
CPC . C12N 9/88; C12N 9/93; C12N 15/74; C12N 1/20; C12P 7/24; C12P 7/26; C12Y 401/02041; C12Y 402/01101; C12Y 602/01034; C07C 47/58
See application file for complete search history.

(56) References Cited

U.S. PATENT DOCUMENTS

| | | | | |
|---|---|---|---|---|
| 6,808,925 | B2 * | 10/2004 | Calos ...................... | C12N 9/00 435/183 |
| 7,981,646 | B2 * | 7/2011 | Heald ...................... | C12P 7/24 435/156 |
| 8,344,119 | B2 * | 1/2013 | Lambert .............. | C12N 9/0006 435/146 |
| 2003/0092143 | A1 | 5/2003 | Rabenhorst et al. | |
| 2014/0087428 | A1 | 3/2014 | Lambrecht et al. | |
| 2016/0312250 | A1 | 10/2016 | Zhou et al. | |

FOREIGN PATENT DOCUMENTS

| | | |
|---|---|---|
| EP | 1 611 244 | 1/2006 |
| EP | 2 721 148 | 4/2014 |
| WO | 01/44480 | 6/2001 |
| WO | 2004/085663 | 10/2004 |
| WO | 2012/172108 | 12/2012 |
| WO | 2015/066722 | 5/2015 |

OTHER PUBLICATIONS

Bibb et al., Cloning and analysis of the promoter region of the erythromycin resistance gene (ermE) of *Streptomyces erythraeus*. Gene, 1985, vol. 38 (1-3): 215-226 (Year: 1985).*
Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Fischer et al., Characterization of promoter region of the enolase-encoding gene enol from anaerobic fungus *Neocallimastix frontalis*: sequence and promoter analysis. Curr Genet., 1995, vol. 28: 80-86. (Year: 1995).*
Satola et al., Binding of Spo0A stimulates spoIIG promoter activity in *Bacillus subtilis*. J. Bacteriol., 1992, vol. 174(5): 1448-1453. (Year: 1992).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650 (Year: 1999).*
Yang et al., Characterization of two Streptomyces enzymes that convert ferulic acid to vanillin. PLOS One , 2013, vol. 8(6), e67339: 1-9. (Year 2013).*

(Continued)

*Primary Examiner* — Ganapathirama Raghu
(74) *Attorney, Agent, or Firm* — Duane Morris LLP; Thomas J. Kowalski; Deborah L. Lu

(57) ABSTRACT

The invention relates to an *Amycolatopsis* strain derived from the *Amycolatopsis* Zyl 926 strain having at least one additional copy of the FCS and ECH genes encoding feruloyl-CoA-synthetase and enoyl-CoA-hydratase/aldolase integrated at the integration site of the φC31 phage. The invention also relates to the method for producing such strains, the integration cassette of the FCS and ECH genes, the use of said strains in a method for producing vanillin, and a method for producing vanillin.

15 Claims, No Drawings

Specification includes a Sequence Listing.

(56) References Cited

OTHER PUBLICATIONS

International Search Report and Written Opinion of the International Searching Authority dated Jan. 19, 2017, which issued during prosecution of International Application No. PCT/FR2016/052403.
Bibb, et al. "The mRNA for the 23S rRNA methylase encoded by the ermE gene of Saccharopolyspora erythraea is translated in the absence of a conventional ribosome-binding site" Molecular Microbiology, 1994, 14(3):533-545.
Keravala, et al. "Site-Specific Chromosomal Integration Mediated by ϕC31 Integrase" Methods in Molecular Biology, 2008, 435:165-173.
Kieser, et al. "Introduction of DNA into Streptomyces" Practical Streptomyces Genetics, Chapter 10, 2000, The John Innes Foundation, pp. 230-252.

* cited by examiner

BACTERIAL STRAINS FOR THE PRODUCTION OF VANILLIN

RELATED APPLICATIONS AND INCORPORATION BY REFERENCE

The present patent application is filed pursuant to 35 U.S.C. § 371 as a U.S. National Phase Application of International Patent Application No. PCT/FR2016/052403 filed Sep. 22, 2016, claiming the benefit of priority to French Patent Application No. 1559142 filed Sep. 29, 2015. The International Application was published as WO 2017/055712 on Apr. 6, 2017. The contents of each of the aforementioned patent applications are herein incorporated by reference in their entirety.

SEQUENCE LISTING

The instant application contains a Sequence Listing which has been submitted electronically in ASCII format and is hereby incorporated by reference in its entirety. Said ASCII copy, created on Mar. 16, 2018, is named 44980002023_SL.txt and is 16,194 bytes in size.

FIELD OF INVENTION

The present invention relates to the field of production of vanillin. It relates particularly to an *Amycolatopsis* strain derived from the *Amycolatopsis* Zyl 926 strain, the preparation process thereof, and the integration cassette thereof.

TECHNICAL BACKGROUND

Vanillin is one of the major components constituting vanilla extract, which is a powerful natural aroma obtained from the bean of an orchid. The extraction of this molecule from vanilla beans is very expensive; the quantities produced are limited and do not cover market demand. Other ways of obtaining vanillin have been sought.

It is for example possible to obtain vanillin from ferulic acid by bioconversion reaction with bacteria. In this patent application, we are interested only in the ferulic acid bioconversion pathway of vanillin by bacteria.

Vanillin production by bacteria is done by deacetylation of ferulic acid by means of the following 3 steps:

1. Activation of ferulic acid in feruloyl-CoA, activation being catalysed by an enzyme, the feruloyl-CoA ligase, hereinafter FCS;
2. Hydroxylation of the feruloyl-CoA in 4-Hydroxy-3-methoxyphenyl-P-hydroxypropionyl-CoA, hydroxylation being catalysed by an enzyme, Enoyl-CoA Hydratase/Aldolase, hereinafter ECH;
3. Deacetylation of the 4-Hydroxy-3-methoxyphenyl-β-hydroxypropionyl-CoA allowing vanillin to be obtained, also catalyzed by the enzyme ECH.

The vanillin obtained can subsequently be oxidized to vanillic acid by an enzyme, vanillin dehydrogenase, hereinafter VDH. However, converting vanillin to vanillic acid is not desired because only the vanillin has the desired aromatic characteristics.

According to the EC nomenclature of the enzymes (Enzyme Commission number):
the enzyme FCS has the code EC 6.2.1.34,
the enzyme ECH has the codes EC 4.2.1.101 and EC 4.1.2.41,
the enzyme VDH has the code EC 1.2.1.67.

EP 2 721 148 A1 describes a microorganism of the genus *Amycolatopsis* not comprising the gene encoding the VDH, said microorganism making it possible to produce vanillin from ferulic acid.

EP 1 611 244 A1 describes a vanillin production process that does not use organic solvents during purification, as they are now considered undesirable in the food industry, to obtain a vanillin called "natural." During said vanillin production process, the biotransformation of ferulic acid into vanillin is performed by the *Amycolatopsis* strain IMI390106, also called the Zyl 926 strain or the *Amycolatopsis* Zyl 926 strain.

The book "Practical *Streptomyces* Genetics", 2000, Kieser, et al. published by The John Innes Foundation, ISBN 0-7084-0623-8, in Chapter 10, describes a method of transfer between *Escherichia coli* and *Streptomyces* for DNA integration at specific sites.

However, the strains of the prior art used in the bioconversion reaction do not allow an optimal conversion of ferulic acid to vanillin. Given the cost of ferulic acid, there remains a need for new strains of bacteria ensuring better conversion of ferulic acid to vanillin.

SUMMARY OF THE INVENTION

The applicant has thus developed new strains of bacteria through an original transformation method, allowing for an improved molar yield during the bioconversion reaction.

The invention thus provides an *Amycolatopsis* strain derived from the *Amycolatopsis* Zyl 926 strain, having at least one additional copy of FCS and ECH genes integrated at the integration site of the phage φC31.

The invention also relates to a method for obtaining an *Amycolatopsis* strain derived from the *Amycolatopsis* Zyl 926 strain by interspecific transfer.

The invention also relates to an integration cassette comprising the expression cassette of ECH genes and FCS.

The invention also relates to the use of said strains in a process for obtaining vanillin.

The invention also relates to a vanillin production process.

DEPOSITS

The Deposits with the Collection Nationale de Cultures de Microorganismes [National Collection of Microorganism Cultures] (CNCM), under deposit accession numbers I-4922, I-4923, and I-4924 were made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION

The present invention relates to novel bacterial strains of the *Amycolatopsis* genus particularly useful for the bioconversion reaction of ferulic acid to vanillin.

After extensive research, the inventors have developed new *Amycolatopsis* strains derived from *Amycolatopsis* Zyl 926 strain to have an improved molar yield compared to the prior art, for the bioconversion reaction of ferulic acid to vanillin through overexpression of FCS and ECH genes into the genome of the 926 *Amycolatopsis* Zyl strain.

A bioconversion molar yield is defined as the ratio between the number of moles of the product obtained, in our case vanillin, divided by the number of moles of substrate implemented, in this case, ferulic acid. When in percentage, this ratio is multiplied by 100.

"Improved molar yield compared to the prior art" means a molar yield of bioconversion greater than or equal to 80%, preferably greater than or equal to 85%, and more preferably equal to greater than 90%.

The *Amycolatopsis* Zyl 926 strain was filed with the CABI Bioscience, UK science centre in Egham, under the number IMI 390106 on 2 Mar. 2003.

The terms "Zyl 926 strain", "926 *Amycolatopsis* Zyl strain," "*Amycolatopsis* IMI 390106 strain," "*Amycolatopsis* strain filed with the CABI Bioscience under number IMI 390106" are here synonymous.

"*Amycolatopsis* strain(s) derived from the strain *Amycolatopsis* Zyl 926" means all strains obtained after transformation of the Zyl 926 strain by interspecific transfer for integrating at least one additional copy of FCS and ECH genes.

The inventors have further demonstrated that new strains of the invention can also improve productivity and consumption of almost all of the ferulic acid in the bioconversion reaction.

"Consuming substantially all of the ferulic acid" means that at least 98% of ferulic acid is consumed during the bioconversion reaction, preferably at least 99%, and even more preferably 100%.

The present invention therefore relates to an *Amycolatopsis* strain derived from the *Amycolatopsis* Zyl 926 strain comprising:
  at least one additional copy of the FCS gene encoding Feruloyl-CoA Synthetase having the protein sequence SEQ ID NO: 1 or any sequence at least 80%, preferably at least 90%, and more preferably at least 95% identical to SEQ ID NO: 1, and
  at least one additional copy of the ECH gene encoding Enoyl-CoA Hydratase/Aldolase having the protein sequence SEQ ID NO: 2 or any sequence at least 80%, preferably at least 90%, and more preferably at least 95% identical to SEQ ID NO: 2,
  said additional copies of genes FCS and ECH being specifically integrated at the integration site of the phage φC31, also called attB site.

The article by Keravala et al. (Methods Mol Biol. 2008) mentions the use of the phage φC31 integrase as a mediator for chromosomal integration site-specific. It thus allows a unidirectional recombination between two att sites called attP and attB.

"Extra copy of the gene" means any copy of an integrated gene of interest into the genome of a strain as well as copies of the gene of interest initially present in the genome.

A protein sequence or nucleic called identical to another when the alignment between the two sequences is perfect, i.e. when there is a perfect correspondence respectively between amino acids or nucleic acids of each sequence.

The sequence identity percentage is calculated by giving a score of 0 or 1 for each amino acid or base sequence as to whether there is identity or not.

The terms "ECH gene encoding Enoyl-CoA Hydratase/Aldolase" and "FCS gene encoding Feruloyl-CoA Synthetase" should not be narrowly interpreted but should also encompass sequences encoding functional variants of these enzymes.

Typically, functional variants of these enzymes FCS and ECH have a protein sequence having an identity percentage of at least 80%, preferably at least 90% and more particularly preferably at least 95% with the protein sequences SEQ ID NO: 1 and SEQ ID NO: 2.

Advantageously, the present invention relates to an *Amycolatopsis* strain wherein additional copies of FCS and ECH genes are placed under the control of the strong ermE* promoter associated with a ribosome binding site, called RBS.

The ermE* promoter is the ermE promoter modified to give a strong and constitutive expression.

The ermE* promoter has nucleic acid sequence SEQ ID NO: 6 or any sequence at least 90%, preferably at least 95% and even more preferably at least 99% identical to SEQ ID NO: 6.

The sequence of the ermE* promoter is described in the article by Bibb et al. (Mol Microbiol. 1994 November; 14(3):533-45)

To obtain the new original strains of the invention that overexpress the FCS and ECH genes, the inventors revealed after much research and experimentation that the interspecific transfer method enabled transformants to be obtained that have integrated at least one supplementary copy of the genes ECH and FCS and that the success of this gene integration method was locus dependent.

The term "locus dependent" means that supplementary copies of genes of interest must be specifically integrated at the φC31 phage integration site.

The present invention therefore relates to a process for obtaining an *Amycolatopsis* strain derived from the *Amycolatopsis* Zyl 926 strain as described above, comprising the steps of:
  a) amplification by PCR of the FCS genes encoding Feruloyl-CoA Synthetase having the sequence SEQ ID NO: 1 or any sequence at least 80%, preferably at least 90%, and more preferably at least 95% identical to SEQ ID NO: 1 and ECH encoding Enoyl-CoA Hydratase/Aldolase having the sequence SEQ ID NO: 2 or any sequence at least 80%, preferably at least 90%, and even more preferably at least 95% identical to SEQ ID NO: 2, isolated from an *Amycolatopsis* strain;
  b) constructing a vector carrying the nucleic acid sequences obtained in step a, from pSET152 plasmid having:
    i. the int gene encoding phage φC31 integrase having the sequence of nucleotide sequence SEQ ID NO: 3 or any sequence at least 80%, preferably at least 90%, and more preferably at least 95% identical to the sequence SEQ ID NO: 3,
    ii. phage binding site φC31 hereinafter attP site with the nucleotide sequence SEQ ID NO: 4, and
    iii. the functional origin of transfer oriT with the nucleotide sequence SEQ ID NO: 5 or any sequence at least 90%, preferably at least 95% and even more preferably at least 99% identical to the sequence SEQ ID NO: 5;
  c) transformation by electroporation of the ET12567 *Escherichia coli* strain with a transferring plasmid comprising all of the genes encoding the transfer machinery the origin of transfer oriT of which was rendered non-functional, and the vector was constructed in step b;
  d) selection of the ET12567 *Escherichia coli* strains transformed in step c by culture in a medium containing neomycin and beta-lactam;

e) interspecific transfer between ET12567 *Escherichia coli* strains transformed and selected in steps c and d and the strain *Amycolatopsis* Zyl 926, by setting coculture;

f) selection of the *Amycolatopsis* Zyl 926 strains having integrated at least one additional copy of the FCS gene encoding feruloyl-CoA synthetase having the sequence SEQ ID NO: 1 or any sequence at least 80%, preferably at least 90%, and more preferably at least 95% identical to SEQ ID NO: 1 and at least one additional copy of the ECH gene encoding enoyl-CoA hydratase having the sequence SEQ ID NO: 2 or any sequence at least 80%, preferably at least 90%, and more preferably at least 95% identical to SEQ ID NO: 2 according to step e, by culturing on a medium containing apramycin.

The FCS and ECH genes have been isolated and amplified from an *Amycolatopsis* strain by a PCR technique known to those skilled in the art. Due to special features of the *Amycolatopsis* genome, the Phusion® High-Fidelity PCR Master Mix with GC Buffer kit from New England Biolabs was preferably used with the GC Buffer.

The sequences of the primers used are the following sequences:

```
SEQ ID NO: 7: Van-ECH-F:
5' GAAGCTTGAGCGATGCATGAGCACAGC 3'

SEQ ID NO: 8: Van-ECH-R:
5' GTCTAGACTGGTTGCGCACTACTTCTC 3'
```

Preferably the FCS and ECH genes were isolated from the strain *Amycolatopsis* Zyl 926.

The pSET152 plasmid has apramycin resistance.

The vector construction according to step b) is made by cloning additional copies of genes FCS and ECH amplified in step a in pSET152 plasmid (Bierman et al, Gene, 116 (1): 43-49, 1992). The PCR product containing ECH and FCS genes was obtained using as genomic DNA matrix of the strain Zyl926 and Van-ECH-F primer (SEQ ID NO: 7) and Van-ECH-R (SEQ ID NO: 8). The fragment to be integrated was obtained by HindIII digestion (+ Klenow) and XbaI. The HindIII fragments (Klenow+) and XbaI were cloned in the EcoRV and XbaI pSET152 sites.

Int gene means the gene encoding the integrase of phage φC31 with the protein sequence SEQ ID NO: 3 or any sequence at least 80%, preferably at least 90%, and more preferably at least 95% identical to the sequence SEQ ID NO: 3.

The phage attachment site φC31, also called attP site present in the pSET152 plasmid, has the sequence SEQ ID NO: 4.

SEQ ID NO: 4 is the following:

```
GCCCCAACTGGGGTAACCTTTGAGTTCTCTCAGTTGGGG
```

Selecting ET 12567 *Escherichia coli* strains transformed in step c) is performed on the basis of the acquisition by these transformed strains of neomycin resistance and beta-lactam.

Co-culturing for the production of the interspecific transfer of step e), is carried out under conventional conditions known to the person skilled in the art (Bierman et al, 1992 see above) and preferably by bringing into contact for several hours a part of the ET12567 *Escherichia coli* obtained in step d. previously transformed and made ready for transformation, and secondly, *Amycolatopsis* Zyl 926 cells previously synchronized for germination by heating.

The *Escherichia coli* ET12567 strain is ATCC BAA-525 (MacNeil et al, Gene 111. 61-68, 1992).

The selection according to step f) of *Amycolatopsis* Zyl 926 strains having integrated at least one copy of FCS and ECH genes is performed on the basis of the acquisition by these strains of apramycin resistance.

According to a particular embodiment, the invention more particularly relates to a method of obtaining an *Amycolatopsis* strain derived from the *Amycolatopsis* Zyl 926 strain as described above, comprising an additional step b', between steps b and c, amplification and cloning of the strong ermE* promoter in the vector constructed in step b, said ermE* promoter being associated with a ribosome binding site, called RBS.

The ermE* promoter has the sequence SEQ ID NO: 6 or any sequence at least 90%, preferably at least 95% and even more preferably at least 99% identical to SEQ ID NO: 6.

According to a particular embodiment, the invention particularly relates to a method for obtaining an *Amycolatopsis* strain derived from the *Amycolatopsis* Zyl 926 strain as described above, wherein the conjugating plasmid of step c is the pUZ8002 plasmid described in the book "Practical *Streptomyces* Genetics", 2000, Kieser, et al, chapter 10, published by The John Innes Foundation, ISBN 0-7084-0623-8, According to a particular embodiment, the invention more particularly relates to a method of obtaining an *Amycolatopsis* strain derived from the *Amycolatopsis* Zyl 926 strain as described above, wherein the beta-lactam from step d is ampicillin.

The present invention also purposes an *Amycolatopsis* strain derived from the *Amycolatopsis* Zyl 926 strain obtainable by the process as defined above.

The present invention also particularly relates to an *Amycolatopsis* strain derived from the strain *Amycolatopsis* Zyl 926, obtainable by the process as defined above, which is selected from the strain filed with the CNCM under the number I-4922, the strain filed with the CNCM under the number I-4923 and the strain filed with the CNCM under the number I-4924.

The strains I-4922, I-4923 and I-4924 are strains of Amycolatopsis sp. filed under the Budapest Treaty, on 11 Dec. 2014 with the CNCM (Collection Nationale de Cultures de Microorganismes [National Collection of Microorganism Cultures]), 25 rue du Docteur Roux, 75724 Paris Cedex 15, France.

The present invention also relates to an integration cassette comprising:

i. an expression cassette of the FCS gene encoding feruloyl-CoA synthetase having the sequence SEQ ID NO: 1 or any sequence at least 80%, preferably at least 90%, and more preferably at least 95% identical to SEQ ID NO: 1 and ECH encoding Enoyl-CoA Hydratase/Aldolase having the sequence SEQ ID NO: 2 or any sequence at least 80%, preferably at least 90%, and even more preferably at least 95% identical to SEQ ID NO: 2;

ii. means for integration of the cassette into the genome of the strain *Amycolatopsis* Zyl 926, including the int gene of the phage φC31 having the sequence SEQ ID NO: 3 or any sequence at least 80%, preferably at least 90%, and more preferably at least 95% identical to the sequence SEQ ID NO: 3 and the φC31 phage attachment site called attP site having the sequence SEQ ID NO: 4;

iii. means for selecting *Escherichia coli* ET12567 strains transformed comprising neomycin and a beta-lactam;

iv. means for selecting *Amycolatopsis* Zyl926 strains having integrated said integration cassette comprising a marker for resistance to apramycin.

An integration cassette is a genetic construct comprising the necessary tools for the integration of one or more genes of interest into the genome of an organism, here the strain *Amycolatopsis* 926 Zyl.

According to a particular embodiment of the invention, the genes encoding Feruloyl-CoA Synthetase and Enoyl-CoA Hydratase/Aldolase of the expression cassette described above are placed under the control of strong ermE* promoter having the sequence SEQ ID NO: 6 or any sequence at least 90%, preferably at least 95% and even more preferably at least 99% identical to SEQ ID NO: 6 said ermE* promoter being associated with a ribosome binding site, also known as RBS.

According to a particular embodiment, the invention more particularly relates to an integration cassette as described above, wherein the beta-lactam is ampicillin.

The invention also relates to the use of new *Amycolatopsis* sp strains derived from the *Amycolatopsis* Zyl 926 strain as described above, in a vanillin production process.

The present invention also relates to a method of producing vanillin comprising the steps of:

a. providing an *Amycolatopsis* strain derived from the *Amycolatopsis* Zyl 926 strain filed with the CABI Bioscience under the number IMI 390106, on 2 Mar. 2003, comprising at least one additional copy of the FCS gene encoding Feruloyl-CoA Synthetase having the sequence SEQ ID sequence NO: 1 or any sequence at least 80%, preferably at least 90%, and more preferably at least 95% identical to SEQ ID NO: 1 and encoding ECH Enoyl-coA Hydratase/Aldolase having the sequence SEQ ID NO: 2 or any sequence at least 80%, preferably at least 90%, and more preferably at least 95% identical to SEQ ID NO: 2 and that said additional copies are specifically incorporated at the φC31 phage integration site;

b. culturing the new *Amycolatopsis* strain derived from step a;

c. bringing ferulic acid into contact with said culture of *Amycolatopsis* strain of step b and incubating same;

d. extracting vanillin from the culture medium.

The cultivation of the new derived *Amycolatopsis* strains is preferably carried out on media containing all the nutrients needed for good growth of the bacteria, including a carbon source at temperatures and pH that are regulated in fermenters.

A source of carbon may be, for example, glycerol.

The incubation according to step c of vanillin production process is carried out until the consumption of substantially all of the ferulic acid and at a temperature between 37° C. and 41° C.

According to a particular embodiment of the invention, the vanillin production process is the process described in EP 1 611 244 A1.

The bioconversion reaction when vanillin production process is therefore carried out in a medium comprising a new *Amycolatopsis* sp. derived from the *Amycolatopsis* Zyl 926 strain according to the invention.

According to a particular embodiment of the invention, the *Amycolatopsis* strain derived from the *Amycolatopsis* Zyl 926 strain used in the vanilla production process in step a is selected from the strain filed with the CNCM under the number I-4922, the strain filed with the CNCM under the number I-4923 and the strain filed with the CNCM under the number I-4924.

The invention more particularly relates to a vanillin production process as described above wherein the molar yield is greater than or equal to 80%, preferably greater than or equal to 85%, and more preferably equal to 90%.

The invention more particularly relates to a vanillin production process as described above wherein at least 98% of ferulic acid is consumed, preferably at least 99%, and more preferably 100%.

The inventors implementing said vanillin production process as described above with the new *Amycolatopsis* strains of the invention have thus surprisingly noticed that:
almost all of the ferulic acid is consumed in the organic reaction conversion;
productivity is improved;
the molar yield is improved;
and this without the flow of vanillin dehydrogenase converting vanillin to vanillic acid being increased.

The present invention also relates to a new *Amycolatopsis* strain as described above in which the gene encoding vanillin dehydrogenase vdh is not removed.

The present invention also relates to a process for obtaining a novel *Amycolatopsis* strain as described above having no step of removing the vdh gene encoding vanillin dehydrogenase.

EXAMPLES

Example 1: Cloning of Additional Copies of the ECH and FCS Genes in Zyl 926 at the φC31 Phage Integration Site Material and Method
Bacterial strains:—*Escherichia coli* ET 12567
*Amycolatopsis* Zyl 926
Plasmids:—p SET152: carrying an ampicillin resistance gene
pUZ8002: carrying a gene for resistance to neomycin.

a. Amplification

The ECH and FCS genes were amplified from the *Amycolatopsis* Zyl 926 strain using the "Phusion® High-Fidelity PCR Master Mix with GC Buffer" kit with GC Buffer.

The primers used are:

```
SEQ ID NO: 7: Van-ECH-F:
5' GAAGCTTGAGCGATGCATGAGCACAGC 3'

SEQ ID NO: 8: Van-ECH-R:
5' GTCTAGACTGGTTGCGCACTACTTCTC 3'
``` b. Cloning

The fragment to be integrated is obtained by HindIII digestion (+ Klenow) and XbaI.

The HindIII fragment (+ Klenow) and XbaI was then cloned in the EcoRV and XbaI sites of pSET152. The plasmid thus obtained is called pLSF01a.

The pSET152 plasmid has the φC31 phage integration system namely:
the int gene encoding the integrase of the φC31 phage;
the attP attachment site of the φC31 phage;

The pSET152 plasmid also has the functional origin of transfer oriT allowing the mobilization thereof and transfer of *E. coli* to *Amycolatopsis* by the strain *E. coli* ET12567+ pUZ8002.

b'. Amplification and Cloning of the ermE* Promoter

The addition of the ermE* promoter and the chloramphenicol resistance gene was carried out by in vivo recombination between short identical sequences (PCR-targeting)

as described by Yu et al. (2000) (Proc Natl Acad Sci USA. 2000 23 May; 97 (11): 5978-83).

For this purpose, a sequence corresponding to the resistance gene for chloramphenicol, the ermE* promoter and the RBS of the tipA gene was obtained by PCR using as matrix the pOSV605 plasmid and as primers the oligonucleotides LG001 and LG002. The sequences of the primers used are following:

SEQ ID NO: 9: LG001:
5' CAGCTATGACATGATTACGAATTCGATAGCTTAGCGATGCTCACGCA

GTTAGACACTCAC 3'

SEQ ID NO: 10: LG002:
5' GCTCCGTCCGGACCCGCCCGTTGCCGACCGCTGTGCTCATATGTCCG

CTCCCTTCTCCCGCGAATTCACTAGTGATT 3'

This yielded a fragment having at each end sequences identical to those of two neighbouring regions on the pLSF01a plasmid:
  one in the part of the vector upstream of the ECH gene, the other at the 5' end of the ECH gene.

The recombination took place in vivo in the strain DY330 (Yu et al. 2000) containing the pLSF01 plasmid after transformation with the PCR product.

Clones that have integrated the ermE* promoter were selected on the basis of the acquisition of chloramphenicol resistance. Selected clones are called pLSF02 plasmids.

c. Transformation

The ET12567 strain containing the pUZ8002 plasmid was transformed by electroporation with the pLSF02 plasmid from steps b. and b'., comprising the additional copies of genes ECH and FCS and strong ermE* promoter associated with the RBS.

d. Selection of Transformants

Selecting transformants having the pLSF02 plasmid is done in a medium containing apramycin.

e. Interspecific Transfer

*Amycolatopsis* Zyl 926 cells are synchronized for germination by heating at 50° C. for 10 minutes.

Transformants (*E. coli* ET12567+pUZ8002+pLSF02) and the *Amycolatopsis* Zyl 926 cells thus prepared are then brought into contact by a co-culture for several hours to carry out the interspecific transfer.

f. Selection of Transformed Zyl 926 Strains

The selection of the *Amycolatopsis* Zyl 926 strains having integrated additional copies of ECH and FCS genes is done in a medium containing apramycin.

Results

This last step has led to the selection of the strains deposited with the CNCM under the numbers I-4922, I-4923, I-4924 and have integrated additional copies of the ECH and FCS genes at the φC31 phage integration site.

Example 2: Cloning of Additional Copies of ECH and FCS Genes in Zyl 926 at the φBTI Phage Integration Site Material and Method
  Bacterial strains:—*Escherichia coli* ET 12567
  *Amycolatopsis* Zyl 926
  Plasmids:—pOSV408: carrying a gene for resistance to kanamycin.
  pUZ8002: carrying a gene for resistance to neomycin.
  a. Amplification The ECH and FCS genes were amplified from the *Amycolatopsis* Zyl 926 strain using the "Phusion® High-Fidelity PCR Master Mix with GC Buffer" kit with GC Buffer The primers used are:

SEQ ID NO: 7: Van-ECH-F:
5' GAAGCTTGAGCGATGCATGAGCACAGC 3'

SEQ ID NO: 8: Van-ECH-R:
5' GTCTAGACTGGTTGCGCACTACTTCTC 3' b. Cloning

The fragment to be integrated is obtained by HindIII digestion (+ Klenow) and XbaI.

The HindIII fragment (+ Klenow) and XbaI was then cloned in the EcoRV and XbaI sites of pOSV408. The plasmid thus obtained is called pLSF01b The pOSV408 plasmid (KanaR) has the integration system of the φBT1 phage namely:
  the int gene encoding integrase of the φBTI phage;
  the attP site of the φBTI attachment phage;

The pOSV408 plasmid also has the functional origin of transfer oriT allowing the mobilization thereof and transfer of *E. coli* to *Amycolatopsis* by the strain *E. coli* ET12567+pUZ8002.

b'. Amplification and Cloning of the ermE* Promoter

The addition of the ermE* promoter and the chloramphenicol resistance gene was carried out by in vivo recombination between short identical sequences (PCR-targeting) as described by Yu et al. (2000) (Proc Natl Acad Sci USA. 2000 May 23; 97 (11): 5978-83).

To this end, a sequence corresponding to the resistance gene for chloramphenicol, the ermE* promoter and for RBS of the tipA gene was obtained by PCR using as matrix the pOSV605 plasmid and as primers the LG001 and LG002 oligonucleotides having respectively the sequences SEQ ID NO: 9 and SEQ ID NO: 10.

This resulted in a fragment having at each end sequences identical to those of two neighbouring regions on the pLSF01b plasmid:
  one in the part of the vector upstream of the ECH gene, the other to the 5' end of the ECH gene.

The recombination took place in vivo in the DY330 strain (Yu et al. 2000) containing the pLSF01b plasmid after transformation by the PCR product.

The clones which have integrated the ermE* promoter were selected on the basis of the acquisition of chloramphenicol resistance. The selected clones are called pLSF07 plasmids.

c. Transformation

The ET12567 strain containing the pUZ8002 plasmid is transformed by electroporation with the pLSF07 plasmid from the preceding steps, comprising the additional copies of the ECH and FCS genes and strong promoter ermE * associated with the RBS.

d. Selection of Transformants

Transformants which have integrated the pLSF07 plasmid are selected in a medium comprising kanamycin.

e. Interspecific Transfer

The cells of *Amycolatopsis* Zyl 926 are synchronized for germination by heating at 50° C. for 10 minutes.

The transformants and *Amycolatopsis* Zyl 926 cells thus prepared are then brought into contact by a co-culture for several hours to carry out the interspecific transfer.

f. Selecting Transformed Zyl 926 Strains

The strains *Amycolatopsis* Zyl 926 having integrated additional copies of the ECH and FCS genes are selected in a medium containing kanamycin.

Results

This last step was used to select the strains filed with the CNCM on 11 Dec. 2014 under number 1-4925, 1-4926 and 1-4927 having integrated additional copies of the FCS and ECH genes at the φBTI phage integration site.

Example 3: Production of Vanillin by the *Amycolatopsis* sp. Strain I-4922

Material and Method
  Bacterial strains:—CNCM-I-4922
  Zyl 926

The vanillin production process used in this example is the process mentioned in EP 1 611 244 A1.

Maximum productivity is calculated using the following equation:

$$\frac{\text{Concentration of the vanillin produced (g/Kg)}}{\text{Elapsed production time (hours)}}$$

The molar yield is calculated according to the following equation:

$$100 \times \frac{\text{vanillin molar concentration}}{\text{ferulic acid molar concentration}}$$

The overall mass yield of vanillin/ferulic acid is calculated according to the following equation:

$$100 \times \frac{\text{vanillin molar concentration}}{\text{ferulic acid mass concentration}}$$

Results

The results obtained using the vanillin production process of EP 1 611 244 with the strain according to the invention I-4922 and the Zyl 926 strain are shown in Table 1 below.

TABLE 1

|  | I-4922 | Zyl 926 (EP 1 611 244) |
| --- | --- | --- |
| Initial ferulic acid concentration | 25.5 g/Kg | 25 g/L |
| Maximum productivity | 0.52 g/Kg · h | Non defined |
| Residual ferulic acid | 0.1 g/Kg | 1.01 g/L |

TABLE 1-continued

|  | I-4922 | Zyl 926 (EP 1 611 244) |
| --- | --- | --- |
| Vanillin produced | 17.1 g/Kg | 13.8 g/L |
| Vanillic acid produced | 0.8 g/Kg | Non defined |
| Molar yield | 86% | 73% |
| Overall vanillin/ferulic acid mass yield | 67% | 55% |

Note that the density is close to 1, the unit g/kg is equivalent to g/L.

Conclusion

The results obtained show that the strain according to the invention I-4922 provides a greater amount of vanillin, an improved molar yield, and the consumption of substantially all of the ferulic acid based on the Zyl 926 strain of the prior art.

Example 4: Comparison of Vanillin Production Using Strains I-4922 and I-4926

Materials and Methods
  Bacterial strains:—CNCM-I-4922 (φC31)
  CNCM-I-4926 (φBT1)
  Zyl 926

The vanillin production process used in this example is the process mentioned of EP 1 611 244 A1.

Results

The results obtained using the vanillin production process of EP 1 611 244 with the strains I-4922, 14926 and Zyl 926 are presented in Table 2 below.

TABLE 2

|  | Zyl 926 | I-4926 | I-4922 |
| --- | --- | --- | --- |
| Initial ferulic acid concentration | 25 g/L | 24.8 g/Kg | 25.5 g/Kg |
| Vanillin produced | 13.8 g/L | 14.4 g/Kg | 17.5 g/Kg |

CONCLUSION

The results show that the strain according to the invention I-4922 having integrated at least one copy of ECH and FCS genes at the φC31 phage integration site enables production of more vanillin compared to the strain of the prior art Zyl 926.

The results also show that the I-4926 strain having incorporated at least one extra copy of the FCS and ECH genes at the φBTI phage integration site does not improve the production of vanillin compared to the Zyl 926 strain of the prior art.

The integration of at least one additional copy of ECH and FCS genes of the invention in the Zyl 926 strain is locus dependent.

The invention claimed is:

1. An *Amycolatopsis* strain obtained after transformation of the *Amycolatopsis* Zyl 926 strain filed with the CABI Bioscience under the number IMI 390106 on 2 Mar. 2003 by interspecific transfer by integrating at least one additional copy of the FCS and at least one additional copy of the ECH gene, the FCS gene encoding feruloyl-CoA-synthetase having the protein sequence SEQ ID NO: 1 or any sequence at least 95% identical to SEQ ID NO: 1, and the ECH gene encoding Enoyl-CoA hydratase/aldolase having the protein sequence SEQ ID NO: 2 or any sequence at least 95% identical to SEQ ID NO: 2 and wherein additional copies of the FCS and ECH genes are specifically integrated at the φC31 phage integration site.

2. An *Amycolatopsis* strain according to claim 1, characterized in that said additional copies of the FCS and ECH genes are placed under the control of ermE* promoter associated with a ribosome combining site.

3. A method for obtaining an *Amycolatopsis* strain obtained after transformation of the *Amycolatopsis* Zyl 926 strain filed with the CABI Bioscience under the number IMI 390106 on 2 Mar. 2003 by interspecific transfer by integrating, at least one additional copy of the FCS gene and at least one additional copy of the ECH gene, the FCS gene encoding feruloyl-CoA-synthetase having the sequence SEQ ID NO: 1 or any sequence encoding feruloyl-CoA-synthetase at least 95% identical to SEQ ID NO: 1, and the ECH gene encoding enoyl-coA hydratase/aldolase having the sequence ID NO: 2 or any sequence encoding enoyl-CoA hydratase/aldolase at least 95% identical to SEQ ID NO: 2 and wherein said additional copies of FCS and ECH genes are specifically integrated at the φC31 phage integration site, comprising the following steps:
   a. PCR amplification of the FCS gene encoding feruloyl-CoA-synthetase having the sequence SEQ ID NO: 1 or any sequence encoding feruloyl-CoA-synthetase at least 95% identical to SEQ ID NO: 1 and of the ECH gene encoding enoyl-CoA hydratase/aldolase having sequence SEQ ID NO: 2 or any sequence encoding enoyl-CoA hydratase/aldolase at least 95% identical to SEQ ID NO: 2, isolated from an *Amycolatopsis* strain;
   b. constructing a vector carrying the nucleic acid sequences obtained in step a, from pSET152 plasmid;
   c. transformation by electroporation of the ET12567 *Escherichia coli* strain with plasmid comprising combining all of the genes encoding the transfer machinery the origin of transfer oriT of which is rendered nonfunctional, and the vector constructed in step b;
   d. selection of strains of *Escherichia coli* ET12567 transformed in step c by culture in a medium containing neomycin and a beta-lactam;
   e. interspecific transfer between *Escherichia coli* ET12567 strains transformed and selected in steps c and d and the *Amycolatopsis* Zyl 926 strain filed with the CABI Bioscience under the number IMI 390106 on 2 Mar. 2003, for implementation in co-culture;
   f selection of *Amycolatopsis* Zyl 926 strains having integratedat least one additional copy of the FCS gene encoding feruloyl-CoA-synthetase having the sequence SEQ ID NO: 1 or any sequence encoding feruloyl-CoA-synthetase having at least 95% identity to SEQ ID NO: 1 and at least one additional copy of the ECH gene encoding enoyl-CoA hydratase/aldolase having the sequence SEQ ID NO: 2 or any sequence encoding enoyl-CoA hydratase/aldolase having at least 95% identity to SEQ ID NO: 2 according to step e, by culturing in a medium containing apramycin.

4. The method according to claim 3, characterized in that it comprises an additional step b' between steps b and c, of amplification and cloning of the ermE* promoter having the nucleic acid sequence of SEQ ID NO: 6, said ermE* promoter being associated with a ribosome binding site.

5. The method according to claim 4, characterized in that the conjugating plasmid of step c is the pUZ8002 plasmid.

6. The method according to claim 3, characterized in that the beta-lactam from step d is ampicillin.

7. The *Amycolatopsis* sp. strain obtained from the *Amycolatopsis* Zyl 926 strain obtainable by the process according to claim 3.

8. The *Amycolatopsis* sp. strain according to claim 1 selected from the strain filed with the CNCM under the number I-4922, the strain filed with the CNCM under the number I-4923 and the strain filed with the CNCM under the number I-4924.

9. An integration cassette characterized in that it comprises:
  i. an expression cassette of the FCS gene encoding feruloyl-CoA-synthetase having the sequence SEQ ID NO: 1 or any sequence encoding feruloyl-CoA-synthetase at least 95% identical to SEQ ID NO: 1, and of the ECH gene encoding enoyl-CoA hydratase/aldolase having the sequence SEQ ID NO: 2 or any sequence encoding enoyl-CoA hydratase/aldolase at least 95% identical to SEQ ID NO: 2;
  ii. means for integration of the cassette into the genome of the strain *Amycolatopsis* Zyl926, comprising the int gene of the φC31 phage having the sequence SEQ ID NO: 3 and the attP attachment site of the φC31 phage having the sequence SEQ ID NO: 4;
  iii. means for selecting transformed *Escherichia coli* ET12567 strains comprising neomycin and a beta-lactam;
  iv. means for selecting *Amycolatopsis* Zyl 926 strains having integrated said integration cassette comprising a marker for resistance to apramycin.

10. The integration cassette according to claim 9, wherein the FCS and ECH genes encoding feruloyl-coA-synthetase and enoyl-coA-hydratase/aldolase of the expression cassette are under the control of the ermE* promoter having the sequence SEQ ID NO: 6, said ermE* promoter being associated with a ribosome binding site.

11. The integration cassette according to claim 9, characterized in that the beta-lactam antibiotic is ampicillin.

12. A method of producing vanillin, wherein the bioconversion reaction is carried out in a medium comprising an *Amycolatopsis* sp. strain obtained after transformation of the *Amycolatopsis* Zyl 926 strain by interspecific transfer according to claim 1.

13. The *Amycolatopsis* strain obtained after transformation of the *Amycolatopsis* Zyl 926 strain filed with the CABI Bioscience under the number IMI 390106 on 2 Mar. 2003 by interspecific transfer by integrating at least one additional copy of the FCS and at least one additional copy of the ECH gene according to claim 1, wherein the FCS gene encoding feruloyl-CoA-synthetase has the protein sequence SEQ ID NO: 1 and the ECH gene encoding enoyl-CoA hydratase/aldolase has the protein sequence SEQ ID NO: 2 and wherein additional copies of the FCS and ECH genes are specifically integrated at the φC31 phage integration site.

14. The method according to claim 3, comprising the following steps:
  a. PCR amplification of the FCS gene encoding feruloyl-CoA-synthetase having the sequence SEQ ID NO: 1 and of the ECH encoding enoyl-CoA hydratase/aldolase having sequence SEQ ID NO: 2, isolated from an *Amycolatopsis* strain;
  b. constructing a vector carrying the nucleic acid sequences obtained in step a, from pSET152 plasmid;
  c. transformation by electroporation of the ET12567 *Escherichia coli* strain with plasmid comprising combining all of the genes encoding the transfer machinery the origin of transfer oriT of which is rendered non-functional, and the vector constructed in step b;
  d. selection of strains of *Escherichia coli* ET12567 transformed in step c by culture in a medium containing neomycin and a beta-lactam;
  e. interspecific transfer between *Escherichia coli* ET12567 strains transformed and selected in steps c and d and the *Amycolatopsis* Zyl 926 strain filed with the CABI Bioscience under the number IMI 390106 on 2 Mar. 2003, for implementation in co-culture;
  f selection of *Amycolatopsis* Zyl 926 strains having integrated at least one additional copy of the FCS gene encoding feruloyl-CoA-synthetase having the sequence SEQ ID NO: 1 and at least one additional copy of the ECH gene encoding enoyl-CoA hydratase/aldolase having the sequence SEQ ID NO: 2 according to step e, by culturing in a medium containing apramycin.

15. The integration cassette according to claim 9, characterized in that it comprises:
  i. an expression cassette of the FCS gene encoding feruloyl-CoA-synthetase having the sequence SEQ ID NO: 1 and of the ECH gene encoding enoyl-CoA hydratase/aldolase having the sequence SEQ ID NO: 2;
  ii. means for integration of the cassette into the genome of the strain *Amycolatopsis* Zyl926, comprising the int gene of the φC31 phage having the sequence SEQ ID NO: 3 and the attP attachment site of the φC31 phage having the sequence SEQ ID NO: 4;
  iii. means for selecting transformed *Escherichia coli* ET12567 strains comprising neomycin and a beta-lactam;
  iv. means for selecting *Amycolatopsis* Zyl 926 strains having integrated said integration cassette comprising a marker for resistance to apramycin.

\* \* \* \* \*

SEQUENCE LISTING

```
<160> NUMBER OF SEQ ID NOS: 10

<210> SEQ ID NO 1
<211> LENGTH: 540
<212> TYPE: PRT
<213> ORGANISM: Amycolatopsis sp.

<400> SEQUENCE: 1

Met Gly Ala Gly Arg Gly Leu Pro Leu Arg Gln Ala Arg Pro Val Pro
1               5                   10                  15
```

-continued

Val Arg Arg Gln Gly Gly Arg Pro Arg Gln Gly Ala Asp Pro Val Pro
            20                  25                  30

Arg Pro Glu Val Leu Pro Ala Arg Pro Glu Arg Leu Arg Pro Gly Glu
        35                  40                  45

Val Val Arg Asn Gln Gly Leu Gly Ser Trp Pro Val Arg Arg Ala Arg
50                  55                  60

Met Ser Pro His Ala Thr Ala Val Arg His Gly Gly Thr Ala Leu Thr
65                  70                  75                  80

Tyr Ala Glu Leu Ser Arg Arg Val Ala Arg Leu Ala Asn Gly Leu Arg
                85                  90                  95

Ala Ala Gly Val Arg Pro Gly Asp Arg Val Ala Tyr Leu Gly Pro Asn
            100                 105                 110

His Pro Ala Tyr Leu Glu Thr Leu Phe Ala Cys Gly Gln Ala Gly Ala
        115                 120                 125

Val Phe Val Pro Leu Asn Phe Arg Leu Gly Val Pro Glu Leu Asp His
130                 135                 140

Ala Leu Ala Asp Ser Gly Ala Ser Val Leu Ile His Thr Pro Glu His
145                 150                 155                 160

Ala Glu Thr Val Ala Ala Leu Ala Ala Gly Arg Leu Leu Arg Val Pro
                165                 170                 175

Ala Gly Glu Leu Asp Ala Ala Asp Glu Pro Pro Asp Leu Pro Val
            180                 185                 190

Gly Leu Asp Asp Val Cys Leu Leu Met Tyr Thr Ser Gly Ser Thr Gly
        195                 200                 205

Arg Pro Lys Gly Ala Met Leu Thr His Gly Asn Leu Thr Trp Asn Cys
210                 215                 220

Val Asn Val Leu Val Glu Thr Asp Leu Ala Ser Asp Glu Arg Ala Leu
225                 230                 235                 240

Val Ala Ala Pro Leu Phe His Ala Ala Leu Gly Met Val Cys Leu
                245                 250                 255

Pro Thr Leu Leu Lys Gly Gly Thr Val Ile Leu His Ser Ala Phe Asp
            260                 265                 270

Pro Gly Ala Val Leu Ser Ala Val Glu Gln Glu Arg Val Thr Leu Val
        275                 280                 285

Phe Gly Val Pro Thr Met Tyr Gln Ala Ile Ala Ala His Pro Arg Trp
290                 295                 300

Arg Ser Ala Asp Leu Ser Ser Leu Arg Thr Leu Leu Cys Gly Gly Ala
305                 310                 315                 320

Pro Val Pro Ala Asp Leu Ala Ser Arg Tyr Leu Asp Arg Gly Leu Ala
                325                 330                 335

Phe Val Gln Gly Tyr Gly Met Thr Glu Ala Ala Pro Gly Val Leu Val
            340                 345                 350

Leu Asp Arg Ala His Val Ala Glu Lys Ile Gly Ser Ala Gly Val Pro
        355                 360                 365

Ser Phe Phe Thr Asp Val Arg Leu Ala Gly Pro Ser Gly Glu Pro Val
370                 375                 380

Pro Pro Gly Glu Lys Gly Glu Ile Val Val Ser Gly Pro Asn Val Met
385                 390                 395                 400

Lys Gly Tyr Trp Gly Arg Pro Glu Ala Thr Ala Glu Val Leu Arg Asp
                405                 410                 415

Gly Trp Phe His Ser Gly Asp Val Ala Thr Val Asp Gly Asp Gly Tyr
            420                 425                 430

Phe His Val Val Asp Arg Leu Lys Asp Met Ile Ile Ser Gly Gly Glu
            435                 440                 445

Asn Ile Tyr Pro Ala Glu Val Glu Asn Glu Leu Tyr Gly Tyr Pro Gly
450                 455                 460

Val Glu Ala Cys Ala Val Ile Gly Val Pro Asp Pro Arg Trp Gly Glu
465                 470                 475                 480

Val Gly Lys Ala Val Val Pro Ala Asp Gly Ser Arg Ile Asp Gly
                485                 490                 495

Asp Glu Leu Leu Ala Trp Leu Arg Thr Arg Leu Ala Gly Tyr Lys Val
                500                 505                 510

Pro Lys Ser Val Glu Phe Thr Asp Arg Leu Pro Thr Thr Gly Ser Gly
            515                 520                 525

Lys Ile Leu Lys Gly Glu Val Arg Arg Phe Gly
530                 535                 540

<210> SEQ ID NO 2
<211> LENGTH: 287
<212> TYPE: PRT
<213> ORGANISM: Amycolatopsis sp.

<400> SEQUENCE: 2

Met Ser Thr Ala Val Gly Asn Gly Arg Val Arg Thr Glu Pro Trp Gly
1               5                   10                  15

Glu Thr Val Leu Val Glu Phe Asp Glu Gly Ile Ala Trp Val Met Leu
            20                  25                  30

Asn Arg Pro Asp Lys Arg Asn Ala Met Asn Pro Thr Leu Asn Asp Glu
        35                  40                  45

Met Val Arg Val Leu Asp His Leu Glu Gly Asp Asp Arg Cys Arg Val
50                  55                  60

Leu Val Leu Thr Gly Ala Gly Glu Ser Phe Ser Ala Gly Met Asp Leu
65                  70                  75                  80

Lys Glu Tyr Phe Arg Glu Val Asp Ala Thr Gly Ser Thr Ala Val Gln
                85                  90                  95

Ile Lys Val Arg Arg Ala Ser Ala Glu Trp Gln Trp Lys Arg Leu Ala
            100                 105                 110

Asn Trp Ser Lys Pro Thr Ile Ala Met Val Asn Gly Trp Cys Phe Gly
        115                 120                 125

Gly Ala Phe Thr Pro Leu Val Ala Cys Asp Leu Ala Phe Ala Asp Glu
130                 135                 140

Asp Ala Arg Phe Gly Leu Ser Glu Val Asn Trp Gly Ile Pro Pro Gly
145                 150                 155                 160

Gly Val Val Ser Arg Ala Leu Ala Ala Thr Val Pro Gln Arg Asp Ala
                165                 170                 175

Leu Tyr Tyr Ile Met Thr Gly Glu Pro Phe Asp Gly Arg Arg Ala Ala
            180                 185                 190

Glu Met Arg Leu Val Asn Glu Ala Leu Pro Ala Asp Arg Leu Arg Glu
        195                 200                 205

Arg Thr Arg Glu Val Ala Leu Lys Leu Ala Ser Met Asn Gln Val Val
    210                 215                 220

Leu His Ala Ala Lys Thr Gly Tyr Lys Ile Ala Gln Glu Met Pro Trp
225                 230                 235                 240

Glu Gln Ala Glu Asp Tyr Leu Tyr Ala Lys Leu Asp Gln Ser Gln Phe
                245                 250                 255

Ala Asp Lys Ala Gly Ala Arg Ala Lys Gly Leu Thr Gln Phe Leu Asp
            260                 265                 270

Gln Lys Ser Tyr Arg Pro Gly Leu Ser Ala Phe Asp Pro Glu Lys
            275                 280                 285

<210> SEQ ID NO 3
<211> LENGTH: 613
<212> TYPE: PRT
<213> ORGANISM: Phage PhiC31

<400> SEQUENCE: 3

Met Thr Gln Gly Val Val Thr Gly Val Asp Thr Tyr Ala Gly Ala Tyr
1               5                   10                  15

Asp Arg Gln Ser Arg Glu Arg Glu Asn Ser Ser Ala Ala Ser Pro Ala
            20                  25                  30

Thr Gln Arg Ser Ala Asn Glu Asp Lys Ala Ala Asp Leu Gln Arg Glu
        35                  40                  45

Val Glu Arg Asp Gly Gly Arg Phe Arg Phe Val Gly His Phe Ser Glu
    50                  55                  60

Ala Pro Gly Thr Ser Ala Phe Gly Thr Ala Glu Arg Pro Glu Phe Glu
65                  70                  75                  80

Arg Ile Leu Asn Glu Cys Arg Ala Gly Arg Leu Asn Met Ile Ile Val
                85                  90                  95

Tyr Asp Val Ser Arg Phe Ser Arg Leu Lys Val Met Asp Ala Ile Pro
            100                 105                 110

Ile Val Ser Glu Leu Leu Ala Leu Gly Val Thr Ile Val Ser Thr Gln
        115                 120                 125

Glu Gly Val Phe Arg Gln Gly Asn Val Met Asp Leu Ile His Leu Ile
    130                 135                 140

Met Arg Leu Asp Ala Ser His Lys Glu Ser Ser Leu Lys Ser Ala Lys
145                 150                 155                 160

Ile Leu Asp Thr Lys Asn Leu Gln Arg Glu Leu Gly Gly Tyr Val Gly
                165                 170                 175

Gly Lys Ala Pro Tyr Gly Phe Glu Leu Val Ser Glu Thr Lys Glu Ile
            180                 185                 190

Thr Arg Asn Gly Arg Met Val Asn Val Val Ile Asn Lys Leu Ala His
        195                 200                 205

Ser Thr Thr Pro Leu Thr Gly Pro Phe Glu Phe Glu Pro Asp Val Ile
    210                 215                 220

Arg Trp Trp Trp Arg Glu Ile Lys Thr His Lys His Leu Pro Phe Lys
225                 230                 235                 240

Pro Gly Ser Gln Ala Ala Ile His Pro Gly Ser Ile Thr Gly Leu Cys
                245                 250                 255

Lys Arg Met Asp Ala Asp Ala Val Pro Thr Arg Gly Glu Thr Ile Gly
            260                 265                 270

Lys Lys Thr Ala Ser Ser Ala Trp Asp Pro Ala Thr Val Met Arg Ile
        275                 280                 285

Leu Arg Asp Pro Arg Ile Ala Gly Phe Ala Ala Glu Val Ile Tyr Lys
    290                 295                 300

Lys Lys Pro Asp Gly Thr Pro Thr Thr Lys Ile Glu Gly Tyr Arg Ile
305                 310                 315                 320

Gln Arg Asp Pro Ile Thr Leu Arg Pro Val Glu Leu Asp Cys Gly Pro
                325                 330                 335

Ile Ile Glu Pro Ala Glu Trp Tyr Glu Leu Gln Ala Trp Leu Asp Gly
            340                 345                 350

Arg Gly Arg Gly Lys Gly Leu Ser Arg Gly Gln Ala Ile Leu Ser Ala

```
            355                 360                 365
Met Asp Lys Leu Tyr Cys Glu Cys Gly Ala Val Met Thr Ser Lys Arg
    370                 375                 380

Gly Glu Glu Ser Ile Lys Asp Ser Tyr Arg Cys Arg Arg Lys Val
385                 390                 395                 400

Val Asp Pro Ser Ala Pro Gly Gln His Glu Gly Thr Cys Asn Val Ser
                405                 410                 415

Met Ala Ala Leu Asp Lys Phe Val Ala Glu Arg Ile Phe Asn Lys Ile
            420                 425                 430

Arg His Ala Glu Gly Asp Glu Thr Leu Ala Leu Leu Trp Glu Ala
435                 440                 445

Ala Arg Arg Phe Gly Lys Leu Thr Glu Ala Pro Glu Lys Ser Gly Glu
        450                 455                 460

Arg Ala Asn Leu Val Ala Glu Arg Ala Asp Ala Leu Asn Ala Leu Glu
465                 470                 475                 480

Glu Leu Tyr Glu Asp Arg Ala Ala Gly Ala Tyr Asp Gly Pro Val Gly
                485                 490                 495

Arg Lys His Phe Arg Lys Gln Gln Ala Ala Leu Thr Leu Arg Gln Gln
            500                 505                 510

Gly Ala Glu Glu Arg Leu Ala Glu Leu Glu Ala Ala Glu Ala Pro Lys
        515                 520                 525

Leu Pro Leu Asp Gln Trp Phe Pro Glu Asp Ala Asp Ala Asp Pro Thr
530                 535                 540

Gly Pro Lys Ser Trp Trp Gly Arg Ala Ser Val Asp Asp Lys Arg Val
545                 550                 555                 560

Phe Val Gly Leu Phe Val Asp Lys Ile Val Val Thr Lys Ser Thr Thr
                565                 570                 575

Gly Arg Gly Gln Gly Thr Pro Ile Glu Lys Arg Ala Ser Ile Thr Trp
            580                 585                 590

Ala Lys Pro Pro Thr Asp Asp Asp Glu Asp Ala Gln Asp Gly Thr
        595                 600                 605

Glu Asp Val Ala Ala
    610

<210> SEQ ID NO 4
<211> LENGTH: 39
<212> TYPE: DNA
<213> ORGANISM: Phage PhiC31

<400> SEQUENCE: 4
gccccaactg gggtaacctt tgagttctct cagttgggg                        39

<210> SEQ ID NO 5
<211> LENGTH: 112
<212> TYPE: DNA
<213> ORGANISM: Sphingobium sp.

<400> SEQUENCE: 5
ccggccagcc tcgcagagca ggattcccgt tgagcaccgc caggtgcgaa taagggacag   60
tgaagaagga acaccgctc gcgggtgggc ctacttcacc tatcctgccc gg          112

<210> SEQ ID NO 6
<211> LENGTH: 1690
<212> TYPE: DNA
<213> ORGANISM: Saccharopolyspora erythraea

<400> SEQUENCE: 6
```

```
ggtaccagcc cgacccgagc acgcgccggc acgcctggtc gatgtcggac cggagttcga    60
ggtacgcggc ttgcaggtcc aggaagggga cgtccatgcg agtgtccgtt cgagtggcgg   120
cttgcgcccg atgctagtcg cggttgatcg gcgatcgcag gtgcacgcgg tcgatcttga   180
cggctggcga gaggtgcggg gaggatctga ccgacgcggt ccacacgtgg caccgcgatg   240
ctgttgtggg ctggacaatc gtgccggttg gtaggatcca gcggtgagca gttcggacga   300
gcagccgcgc ccgcgtcgcc gcaaccagga tcggcagcac cccaaccaga accgccggt    360 gctgggccgt accgagcggg accgcaaccg gcgccagttc gggcagaact tcctccgcga   420
ccgcaagacc atcgcgcgca tcgccgagac agccgagctg cggcccgatc tgccggtgct   480
ggaagccggc cccgtcgaag ggctgctcac cagggaactc gccgaccgcg cgcgtcaggt   540
gacgtcgtac gagatcgacc cccggctggc gaagtcgttg cggagaaagc tttccggcca   600
cccgaacatc gaagtcgtca acgccgactt cctcaccgcc gaaccgccgc cgagccgtt    660 cgccttcgtc ggcgcgatcc cctacggcat cacctcggcg atcgtggact ggtgcctgga   720
ggcgccgacg atcgagacgg cgacgatggt cacgcagctg gagttcgccc ggaagcggac   780
cggcgattac ggccgctgga ccgcctcac ggtgatgacc tggccgctgt tcgagtggga    840
gttcgtcgag aaggtcgact cggcgatcat gcggctgcgc aggcgcgccg aaccgctgct   900
ggaaggcgcg cgcgctcgaac gctacgagtc gatggtcgag ctgtgcttca ccggcgtcgg   960
cggcaacatc caggcgtcgc ttctgcgcaa gtacccgagg cgccgcgtcg aggcggcgtt  1020
cgaccacgcg ggggtcgggg gcggcgccgt ggtcgcctac gtccggccgg agcagtggct  1080
ccggctgttc gagcggctgg atcagaagaa cgaaccgagg ggtgggcagc cccagcgggg  1140
caggcgaacc ggcggacggg accacgggga ccggcgaacc ggcgggcagg atcgcggcga  1200
tcggcgaacc ggcggccgcg accacaggga ccggcaagcc agcggccacg gcgatcgtcg  1260
cagcagcgga cgcaatcgcg acgacggacg aaccggcgag cgcgagcagg gggaccaagg  1320
cgggcggcgg gggccgtccg ggggtggacg gaccggcgga cgtccagggc gacgcggcgg  1380
acccgggcag cggtagtccc cggcacgcgc aacgcggcag gccgtcgagc ggcctgcccc  1440
gttctgtcga gaggaatcag aggttgatgt cggcccggag gtcgatgtcg cgcgacgacg  1500
agccgatctc caccgctcgc ttgccgcccc cgagcttcca gccgcccgcg gcttcgtccc  1560
agtgctggag ggccgctccg cgacgtgcac ccggacgcgc ttggtctcgc ccggtgcgag  1620
ttcgaccttc tggtacccgg cgagctgtaa atctgccggc tcagccttcc caggttcgaa  1680
tcctggcgcc                                                         1690
```

```
<210> SEQ ID NO 7
<211> LENGTH: 27
<212> TYPE: DNA
<213> ORGANISM: Artificial Sequence
<220> FEATURE:
<223> OTHER INFORMATION: Amorce PCR

<400> SEQUENCE: 7
gaagcttgag cgatgcatga gcacagc                                        27

<210> SEQ ID NO 8
<211> LENGTH: 27
<212> TYPE: DNA
<213> ORGANISM: Artificial Sequence
<220> FEATURE:
<223> OTHER INFORMATION: Amorce PCR
```

```
<400> SEQUENCE: 8
gtctagactg gttgcgcact acttctc                                               27

<210> SEQ ID NO 9
<211> LENGTH: 60
<212> TYPE: DNA
<213> ORGANISM: Artificial Sequence
<220> FEATURE:
<223> OTHER INFORMATION: Amorce PCR

<400> SEQUENCE: 9
cagctatgac atgattacga attcgatagc ttagcgatgc tcacgcagtt agacactcac          60

<210> SEQ ID NO 10
<211> LENGTH: 77
<212> TYPE: DNA
<213> ORGANISM: Artificial Sequence
<220> FEATURE:
<223> OTHER INFORMATION: Amorce PCR

<400> SEQUENCE: 10
gctccgtccg gacccgcccg ttgccgaccg ctgtgctcat atgtccgctc ccttctcccg          60
cgaattcact agtgatt                                                         77
```